United States Patent [19]

Heaston

[11] Patent Number: 5,037,436

[45] Date of Patent: Aug. 6, 1991

[54] BREAST PROSTHESIS AND SUPPORT THEREFOR

[76] Inventor: Sharon K. Heaston, 300 W. 123rd, #2512, Westminster, Colo. 80234

[21] Appl. No.: 487,215

[22] Filed: Mar. 1, 1990

[51] Int. Cl.[5] .............................................. A61F 2/52
[52] U.S. Cl. ..................................... 623/7; 206/438; 128/DIG. 20; A61F/2/52
[58] Field of Search ................. 128/78, 402, DIG. 20, 128/400; 623/7, 8; 206/438, 366, 278; 441/59, 66, 81, 129, 130, 88, 122, 125; 5/436, 446, 441

[56] References Cited

U.S. PATENT DOCUMENTS

| | | | |
|---|---|---|---|
| 3,094,723 | 6/1963 | Manhart | 441/88 |
| 3,135,978 | 6/1964 | Grasmoen | 441/66 |
| 3,301,260 | 1/1967 | Ray | 623/7 X |
| 3,332,415 | 7/1967 | Ericson | 441/122 X |
| 3,338,237 | 8/1967 | Sconce | 128/DIG. 20 X |
| 3,765,412 | 10/1973 | Ommaya et al. | 128/DIG. 20 X |
| 3,820,179 | 6/1974 | Maertin | 441/122 |
| 3,902,456 | 9/1975 | David | 5/436 X |
| 3,967,335 | 7/1976 | Rhoads | 5/436 |
| 4,054,960 | 10/1977 | Pettit et al. | 5/446 |
| 4,103,147 | 7/1978 | Carvalho | 128/400 X |
| 4,190,040 | 2/1980 | Schulte | 623/8 X |
| 4,236,264 | 12/1980 | Britzman | 5/441 X |
| 4,600,551 | 7/1986 | Erb | 623/7 X |
| 4,671,507 | 6/1987 | Huttner | 441/122 X |

Primary Examiner—Richard J. Apley
Assistant Examiner—Linda C. M. Dvorak
Attorney, Agent, or Firm—Gary M. Polumbus

[57] ABSTRACT

A portable support for a breast prosthesis includes in two disclosed embodiments an inflatable bladder of a closed loop configuration with the bladder being made of a flexible material and including valve means whereby the bladder can be selectively inflated and deflated. The bladder in its inflated condition serves to circumferentially and substantially uniformly engage and support the prosthesis without substantially deforming the prosthesis.

9 Claims, 3 Drawing Sheets

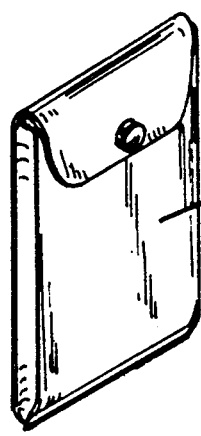
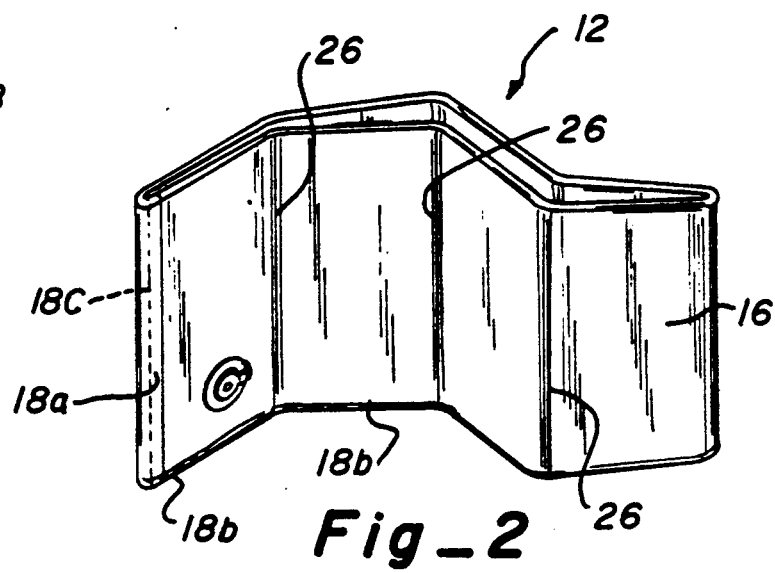
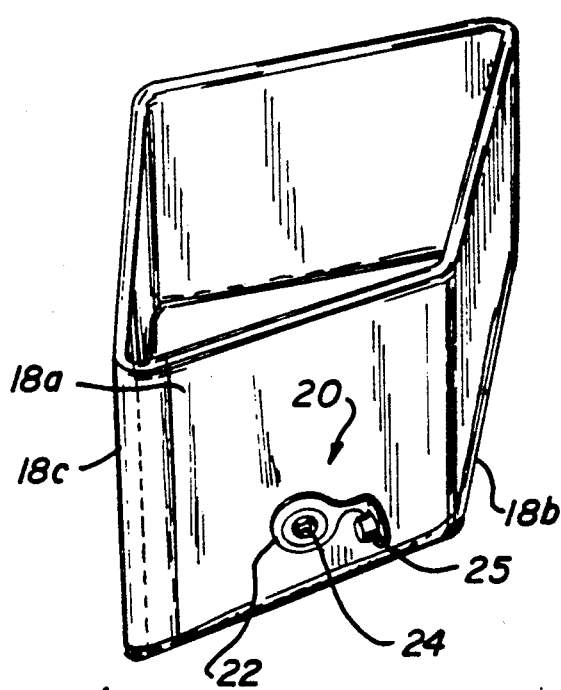
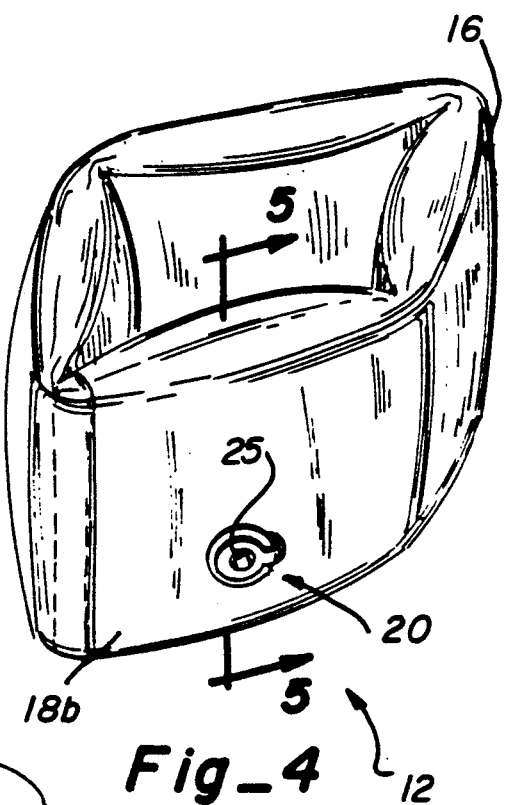
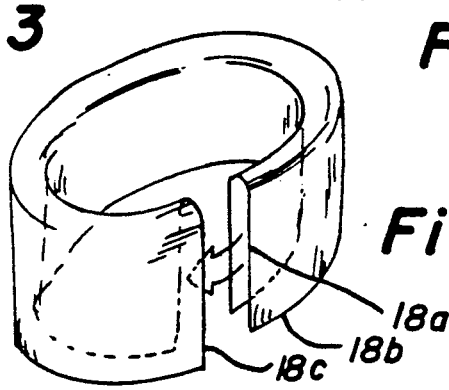

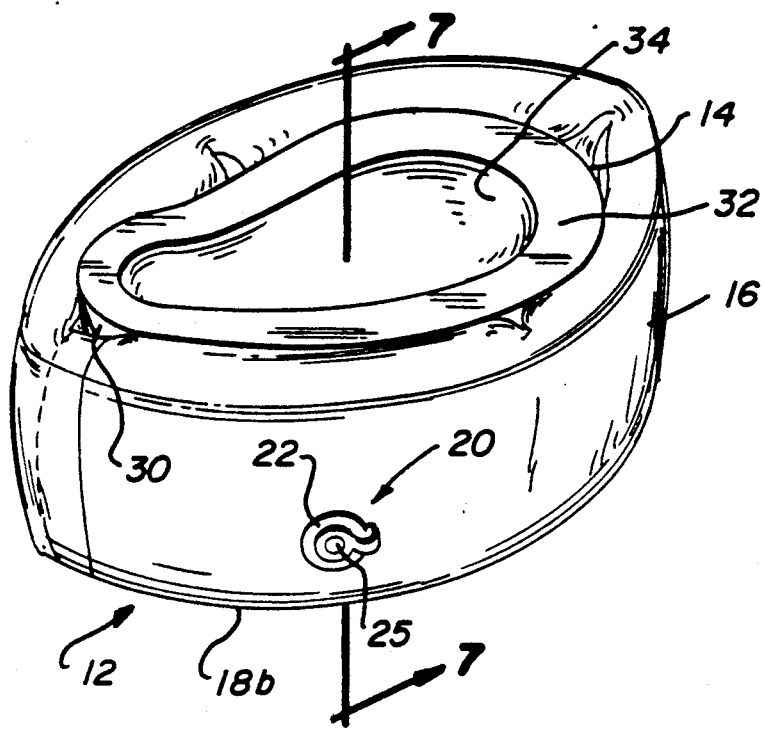
Fig_6
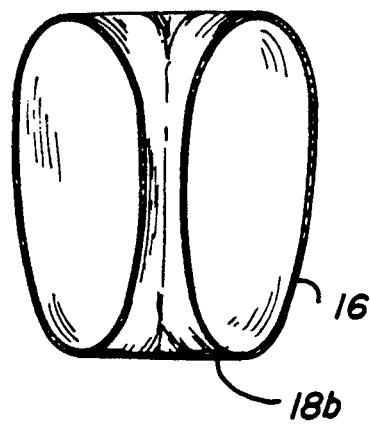
Fig_5
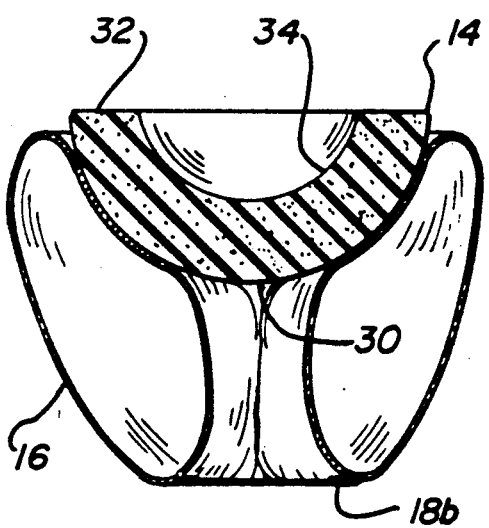
Fig_7
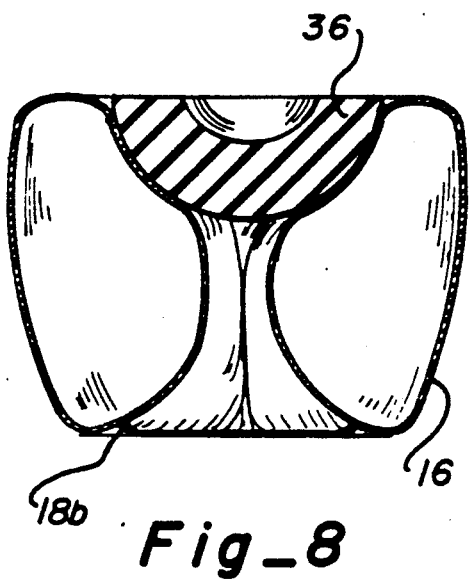
Fig_8

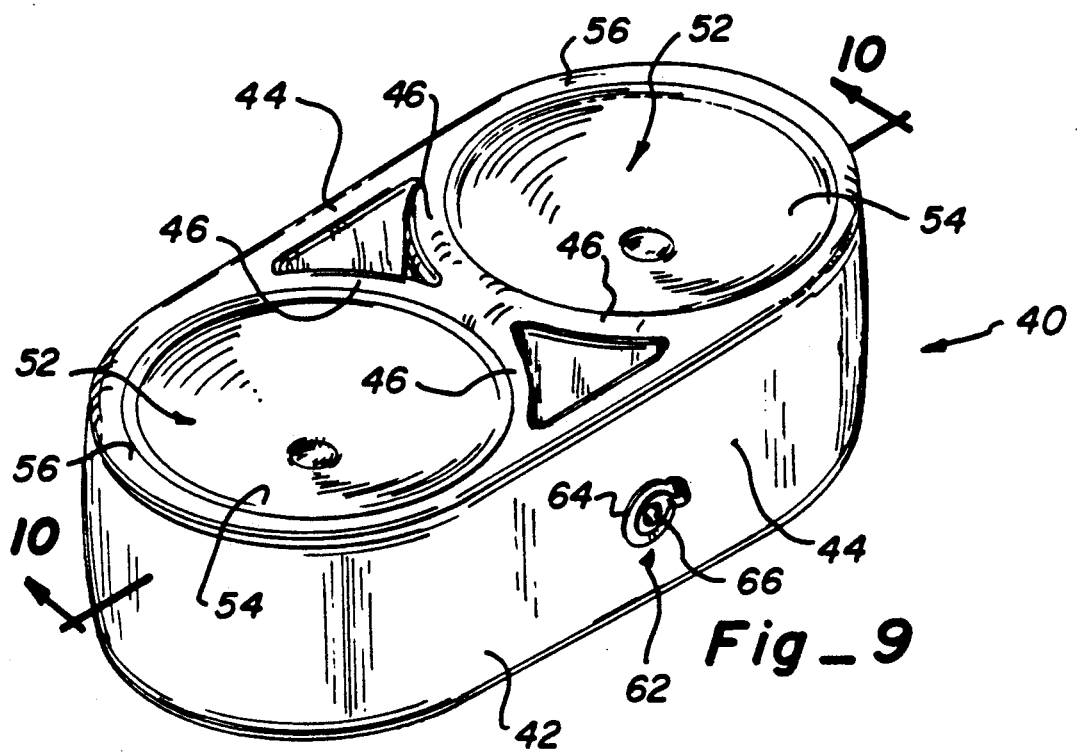
Fig_9
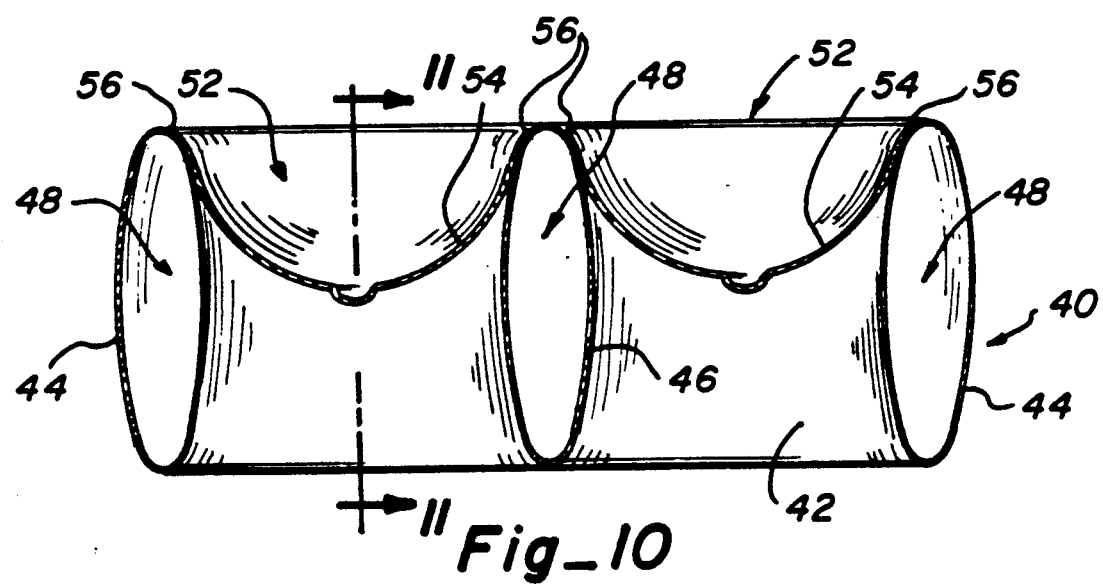
Fig_10
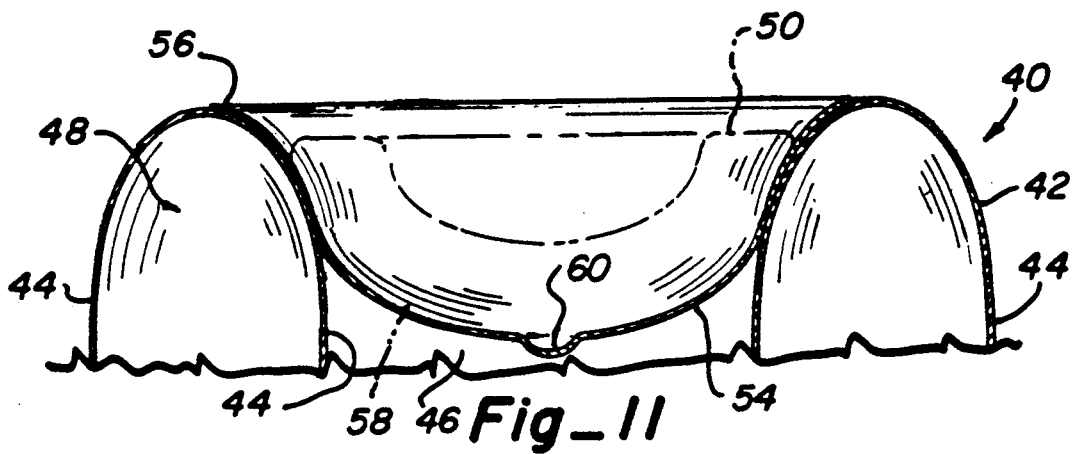
Fig_11

BREAST PROSTHESIS AND SUPPORT THEREFOR

BACKGROUND OF THE INVENTION

1. Field Of The Invention

The present invention relates generally to breast prostheses and more particularly to a portable support for such prostheses wherein a prosthesis can be supported and retained without deformation.

2. Description Of The Prior Art

A typical breast prosthesis worn after a mastectomy is made of a material simulating the glandular material in a human female breast. The prosthesis may be characterized as having gelatinous physical behavioral characteristics. In other words, the prosthesis is flowable within limits and, therefore, changes form depending upon its spatial orientation. However, if the prosthesis is allowed to remain deformed for an extended period of time it will no longer resemble the female breast and therefore becomes unsuitable for use.

When the prosthesis is held in place on its user in a conventional manner as with a bra or other undergarment, it assumes a configuration simulating the female breast. It is difficult, however, when not in use to store or support the breast in this orientation and accordingly such prostheses are typically stored nipple down in a rigid container having a cavity molded therein to uniformly support the prosthesis and hold it in a desired configuration to eliminate any possibility of deformation.

The problem with supporting breast prostheses in rigid containers of this conventional type, is that the container itself is of necessity slightly larger than the prosthesis whereby if the user is travelling she must carry a relatively large package in which the prosthesis can be stored overnight. The rigid container type support is therefore not desirable for travel purposes even though for home use it has traditionally been the most desirable form of support for the prosthesis.

The present invention was developed in an attempt to provide a support for a breast prosthesis which was suitable for travel and would retain the prosthesis in a predetermined, non-deformed orientation thereby overcoming the shortcomings in the prior art systems for storing and supporting such prostheses.

SUMMARY OF THE INVENTION

The present invention consists of an inflatable lightweight bladder in a closed loop configuration with the bladder being made of a flexible material and including valve means whereby the bladder can be selectively inflated and deflated. In its inflated configuration, the bladder serves to engage and support a breast prosthesis without substantially deforming the prosthesis. In its deflated condition, the bladder can be folded into a small flat package that is easily carried in ones purse or other travel bag without occupying an undue amount of space.

In one embodiment of the invention the inflated bladder is of an oval or donut-shaped configuration and is adapted to circumferentially engage and support the prosthesis in a nipple down orientation. The bladder is made of a material that is flexible in nature so as to readily conform with the contour of the breast prosthesis but is rigid enough to retain the prosthesis in a non-deformed configuration.

In a second embodiment the bladder is also of generally oval configuration with an inflatable portion of the bladder circumferentially supporting a sheet of soft vacuum formed material on which the prosthesis can be uniformly supported over its entire weight bearing surface.

Other aspects, features and details of the present invention can be more completely understood by reference to the following detailed description of a preferred embodiment, taken in conjunction with the drawings, and from the appended claims.

BRIEF DESCRIPTION OF THE DRAWING

FIG. 1 is a perspective view of a packet in which the support for a breast prosthesis of the present invention can be stored when in a deflated condition.

FIG. 2 is a perspective view of a first embodiment of the support of the present invention in a deflated and unfolded condition.

FIG. 3 is a perspective view of the first embodiment of the support of the present invention in a further unfolded condition as is caused by initial inflation of the support.

FIG. 4 is a perspective view similar to FIG. 3 with the support being further inflated and in a condition ready to receive and support a breast prosthesis.

FIG. 5 is an enlarged fragmentary section taken along line 5—5 of FIG. 4.

FIG. 6 is a perspective view similar to FIG. 4 showing the first embodiment of the support of the present invention in operative relationship with a breast prosthesis.

FIG. 7 is an enlarged section taken along line 7—7 of FIG. 6.

FIG. 8 is a section similar to FIG. 7 illustrating the support in operative relationship with a smaller prosthesis.

FIG. 9 is a perspective view of a second embodiment of the support of the present invention.

FIG. 10 is a section taken along line 10—10 of FIG. 9.

FIG. 11 is an enlarged section taken along line 11—11 of FIG. 10.

FIG. 12 is a schematic view illustrating the manner in which the bladder is formed from a flat sheet of material.

DESCRIPTION OF THE PREFERRED EMBODIMENTS

As is probably best appreciated by reference to FIG. 2., a first embodiment 12 of the support for a breast prosthesis 14 of the present invention can be seen to comprise a bladder 16 that may be formed from a sheet of planar film type material that has been folded and sealed into a continuous loop type configuration. In the preferred embodiment, the bladder 16 is formed from a rectangular sheet or film of air impermeable polyvinylchloride that has been folded along a longitudinal center line so as to define three pairs of adjacent free edges 18a, 18b and 18c. As can be appreciated by reference to FIG. 12, the pair of free edges 18a at one end of the folded sheet are then inserted between the pair of free edges 18c at the opposite end so that the free edges 18a can be hermetically sealed to adjacent free edges 18c. Subsequently the free edges 18b are hermetically sealed together forming a closed loop, airtight body with a continuous but closed air pocket therein. The polyvinylchloride material is flexible in nature but also somewhat rigid for reasons to become more apparent hereinafter.

The bladder 16 includes a valve member 20 which in the preferred form is hermetically sealed into the wall of the bladder at any convenient location and is readily operable to inflate or deflate the bladder as desired. The valve member 20 may be of the type used on many inflatable beach accessories. The valve includes a base 22 having an opening 24 therethrough and an attached plug 25 that is releasably sealable in the opening to selectively hermetically seal the opening.

By reference to FIG. 2, it will be appreciated that the bladder 16 can be folded along the dashed lines 26 into a very compact unit for storage in a portable packet 28 of the type shown in FIG. 1. In this manner, the bladder can be transported in a woman's purse or other travel bag without occupying unnecessary space therein.

By inflating the bladder 16 to the condition illustrated in FIG. 7 and standing the bladder on the sealed edge 18b which forms a closed loop, the support 12 is in a desired cup-like orientation for receiving and supporting a typical breast prosthesis 14 as illustrated in FIG. 7. A conventional breast prosthesis is made of a material that simulates the glandular material of a human female breast and, therefore, may be described as behaving like a gelatinous material. The prosthesis is bulbous in nature simulating the configuration of the female breast and includes a simulated nipple (not seen) formed in an outer curved surface 30 thereof. The reverse side of the prosthesis is defined by a flat wall 32 in which has been formed a large recess 34. While the particular structure of the breast prosthesis is not important to the present invention, its behavioral patterns when placed in various orientations is significantly important.

The inherent nature of the breast prosthesis 14 allows it to take different shapes depending upon its spatial orientation so that when the prosthesis is positioned on a woman's chest and held in place in any suitable manner such as with a bra, it will simulate in configuration the natural human breast of the woman. However, when allowing the prosthesis to be supported on the flat back wall 32 thereof the prosthesis becomes deformed from the configuration assumed when properly supported on a woman's chest and if allowed to remain in this deformed condition, can become permanently deformed so that it is no longer suitable for use as a breast prosthesis. It is known, however, that if the prosthesis is oriented with the flat wall 32 facing upwardly and is adequately supported along the outer curved surface 30 with the nipple directed downwardly, the prosthesis will retain its configuration and remain useful for a long period of time.

Through use of the support 12, and as best illustrated in FIG. 6, a breast prosthesis 14 positioned on the inflated support will be uniformly supported along the circumference and a substantial portion of the outer curved surface 30 to retain the desired configuration of the prosthesis. The support can, therefore, be repeatedly used without deforming the prosthesis. In actual use, the prosthesis will at least slightly deform the support so that the surface of the support that engages the prosthesis assumes a matching or mating configuration to the outer curved surface 30 of the prosthesis.

Of course, in order for the support 12 of the present invention to uniformly and circumferentially support the breast prosthesis 14, it must be made of a desireable material having characteristics that will allow the support to flex and assume the contour of the outer curved surface 30 of the breast prosthesis without allowing the breast prosthesis to become deformed from its desired configuration. A material found desirable and suitable for this purpose is an air impermeable polyvinylchloride film identified as 1076 FR3 and sold by Rick Industries of Uhrichsville, Ohio. The particular material is frosty clear, 6 mils in thickness, and has the following film and physical properties:

| PHYSICAL PROPERTIES | 1076 FR3 METHOD | VALUE |
| --- | --- | --- |
| Durometer (Shore A) | ASTM D 676 | 70 (5.5 S-Hand) |
| Low Temp Flex 'f 'C. | ASTM D 1043 | −40 |
| 24 Hr. Volatility | ASTM D 1203 | 4.0 |
| 100% Modulus (psi) | ASTM D 638 | 900 |
| Tensile Strength (psi) | ASTM D 638 | 2000 |
| % Elongation at Break | ASTM D 638 | 470 |

It will be appreciated that the support 12 is versatile in nature in that not only can it be folded into a compact unit for travel purposes, it can also be inflated to various pressures and made in various sizes to accommodate the different size and weight breast prostheses in use. FIG. 8 illustrates the support 12 in use with a smaller sized breast prosthesis 36 than the breast prosthesis 14 illustrated in FIGS. 6 and 7. The desired pressure of the inflated support 12 is easily obtained with repeated use of the device so that uniform support for a breast prosthesis 14 can be obtained night after night.

A second embodiment 40 of the support of the present invention is illustrated in FIGS. 9 through 11 and can again be seen to be an inflatable bladder but having a different configuration than the support of the first embodiment of the present invention.

The support 40 of the second embodiment of the invention can be seen to comprise an inflatable bladder 42 having an oblong closed loop outer body wall 44 portion with inner body walls 46 cooperating with the outer body wall in defining a substantially figure-eight shaped framework. Both the inner and outer body walls of the bladder are of double-walled construction so as to define a thin continuous space 48 which can be selectively filled with air. Of course, when the bladder is inflated in the condition illustrated in FIGS. 9 through 11, the support 40 is in a condition to retain two breast prostheses 50, only one being shown. When deflated, the bladder can be folded into a compact unit for transportation in a user's purse, pocket or the like.

The outer and inner body walls 44 and 46 respectively of the support define a pair of adjacent support areas 52 which are substantially oval in configuration. A pair of thin membranes 54 are integrated into the support so as to be circumferentially suspended along their perimeters 56 from the outer and inner body walls of the support. While the suspended membranes 54 may be made from the same material as the outer and inner inflatable body walls 44 and 46, the membranes are preferably vacuum formed so as to conform with the shape and configuration of an outer curved surface 58 of the breast prosthesis 50. In other words, the membranes are custom molded for a particular size prosthesis and, therefore, can even include an indentation 60 to accommodate the nipple which is formed in the prosthesis. The membranes are secured to the inflatable inner and outer body walls of the support along their perimeters 56 in any suitable manner such as by dielectric heat sealing, adhesive, or the like.

Depending upon the material used for the membranes, if the material is of a relatively soft nature while still being vacuum formable, the membranes will retain a configuration to function like a cradle in precisely accommodating and uniformly supporting given breast prostheses across their entire weight bearing surfaces when the support is in an inflated condition but will readily fold with the inflatable outer and inner body walls when the support is deflated.

Of course, a conventional valve 62 is provided for inflating and deflating the bladder. This valve may be of the type found on many beach accessories which includes a base 64 having an opening therethrough and an attached plug 66 adapted to be releasably seated in the opening to selectively hermetically seal the opening to retain the support in its inflated condition.

The material previously described as being suitable and desirable for use in the first described embodiment of the present invention would be ideally suited for use in the second embodiment of the invention as well.

It will be appreciated that the general concept employed in both the first and second described embodiments of the present invention can be incorporated into supports for one or two prostheses even though the first described embodiment has been illustrated in conjunction with a support for a single prosthesis while the second described embodiment has been described for use in supporting a pair of prostheses.

Although the present invention has been described with a certain degree of particularity, it is understood that the present disclosure has been made by way of example, and changes in detail or structure may be made without departing from the spirit of invention, as defined in the appended claims.

I claim:

1. The combination of a support and a breast prosthesis wherein the prosthesis is made of a material having generally gelatinous physical behavioral characteristics, said support comprising an inflatable bladder, said bladder being made of a flexible material and including valve means whereby the bladder can be selectively inflated and deflated, the bladder in its inflated condition serving to circumferentially engage, support and substantially maintain the physical configuration of the prosthesis.

2. The combination of claim 1 wherein said bladder is at least slightly deformed in its inflated condition by said prosthesis when in use.

3. The combination of claim 1 wherein said bladder is made from a sheet of flexible air impermeable material having a longitudinal center line, and wherein the material has been folded along the longitudinal center line to define adjacent free edges of the material that are hermetically sealed together to form a closed loop configuration.

4. The combination of claim 1 wherein said bladder in its deflated condition is foldable into a flat orientation.

5. The combination of claim 1 wherein said bladder is made from a sheet of polyvinylchloride.

6. The combination of claim 1 wherein said sheet of polyvinylchloride is a film having the following characteristics:

| PHYSICAL PROPERTIES | METHOD | VALUE |
|---|---|---|
| Durometer (Shore A) | ASTM D 676 | 70 (5.5 S-Hand) |
| Low Temp Flex 'f °C. | ASTM D 1043 | −40 |
| 24 Hr. Volatility | ASTM D 1203 | 4.0 |
| 100% Modulus (psi) | ASTM D 638 | 900 |
| Tensile Strength (psi) | ASTM D 638 | 2000 |
| % Elongation at Break | ASTM D 638 | 470 |

7. The combination of claim 1 further including membrane means affixed to and supported by said bladder forming a cradle in which said prosthesis can be retained.

8. The combination of claim 7 wherein said membrane means is vacuum formed to conform with a portion of said prosthesis whereby said prosthesis can be uniformly supported by said membrane means.

9. The combination of claim 7 wherein said bladder defines a pair of generally oval-shaped areas and wherein there is a membrane means in each of said oval-shaped areas forming cradles in which a pair of said prosthesis can be retained.

* * * * *